United States Patent
Bushi

(10) Patent No.: US 11,382,518 B2
(45) Date of Patent: Jul. 12, 2022

(54) SYSTEM AND METHOD OF DETECTING INTER-VASCULAR OCCLUSION

(71) Applicant: FASTBREAK MEDICAL LTD, Ness Ziona (IL)

(72) Inventor: Doron Bushi, Ness Ziona (IL)

(73) Assignee: FASTBREAK MEDICAL LTD, Ness Ziona (IL)

( * ) Notice: Subject to any disclaimer, the term of this patent is extended or adjusted under 35 U.S.C. 154(b) by 456 days.

(21) Appl. No.: 16/472,904

(22) PCT Filed: Dec. 25, 2017

(86) PCT No.: PCT/IL2017/051381
§ 371 (c)(1),
(2) Date: Jun. 24, 2019

(87) PCT Pub. No.: WO2018/116308
PCT Pub. Date: Jun. 28, 2018

(65) Prior Publication Data
US 2020/0085317 A1    Mar. 19, 2020

Related U.S. Application Data

(60) Provisional application No. 62/439,037, filed on Dec. 25, 2016.

(51) Int. Cl.
*A61B 5/02* (2006.01)
*A61B 5/00* (2006.01)
(Continued)

(52) U.S. Cl.
CPC ........ *A61B 5/02007* (2013.01); *A61B 5/0004* (2013.01); *A61B 5/021* (2013.01);
(Continued)

(58) Field of Classification Search
CPC ... A61B 5/02; A61B 5/02007; A61B 5/02014; A61B 5/6817; A61B 5/6814;
(Continued)

(56) References Cited

U.S. PATENT DOCUMENTS 5,388,583 A * 2/1995 Ragauskas ............. A61B 5/031
600/438
5,840,018 A * 11/1998 Michaeli .................. A61B 8/06
600/300
(Continued)

FOREIGN PATENT DOCUMENTS

WO    WO 2016/019250    2/2016

OTHER PUBLICATIONS

International Search Report of Application No. PCT/IL2017/051381 dated Mar. 29, 2018.
(Continued)

*Primary Examiner* — Oommen Jacob
(74) *Attorney, Agent, or Firm* — Pearl Cohen Zedek Latzer Baratz LLP

(57) ABSTRACT

Some aspects of the invention may be directed to a system and method of determining an occurrence of inter-vascular occlusion. The method may include: receiving, from a first sensor, a first indication, related to blood flow in a first artery supplying blood to a first hemisphere of a subject's brain; receiving from one of: the first sensor and a second sensor, a second indication related to the blood flow in a second artery supplying blood to a second hemisphere of the subject's brain; comparing the first and second indications; and determining an occurrence of an inter-vascular occlusion based on the comparison.

14 Claims, 10 Drawing Sheets

(51) Int. Cl.
  *A61B 5/021*   (2006.01)
  *A61B 5/0265*   (2006.01)
  *A61B 5/107*   (2006.01)
  *A61B 8/06*   (2006.01)
  *A61B 8/08*   (2006.01)

(52) U.S. Cl.
  CPC .......... *A61B 5/0265* (2013.01); *A61B 5/1073* (2013.01); *A61B 5/6803* (2013.01); *A61B 5/6804* (2013.01); *A61B 8/06* (2013.01); *A61B 8/488* (2013.01)

(58) Field of Classification Search
  CPC ..... A61B 5/0295; A61B 5/0261; A61B 5/245; A61B 5/0535; A61B 5/0265; A61B 5/6803
  See application file for complete search history.

(56) References Cited

U.S. PATENT DOCUMENTS

| | | | |
|---|---|---|---|
| 6,268,223 B1 | 7/2001 | Cornell-Bell et al. | |
| 6,387,051 B1* | 5/2002 | Ragauskas | A61B 5/031 600/438 |
| 6,475,155 B2 | 11/2002 | Ogura et al. | |
| 6,612,993 B2 | 9/2003 | Narimatsu | |
| 6,670,138 B2 | 12/2003 | Gonzalez-Zulueta et al. | |
| 6,955,648 B2 | 10/2005 | Mozayeni et al. | |
| 7,024,238 B2 | 4/2006 | Bergethon | |
| 7,202,089 B2 | 4/2007 | kleinfeld | |
| 2002/0103436 A1* | 8/2002 | Njemanze | A61B 8/4281 600/453 |
| 2005/0130230 A1 | 6/2005 | Davalos et al. | |
| 2005/0283070 A1* | 12/2005 | Imielinska | A61B 6/032 600/425 |
| 2007/0225585 A1* | 9/2007 | Washbon | A61B 5/6803 600/393 |
| 2007/0293760 A1* | 12/2007 | Schaafsma | A61B 5/026 600/454 |
| 2008/0097237 A1* | 4/2008 | Gabaldon | A61B 7/001 600/561 |
| 2009/0177279 A1* | 7/2009 | Luciano | A61M 60/135 623/11.11 |
| 2010/0016735 A1* | 1/2010 | Harpas | A61B 5/02125 600/485 |
| 2010/0063405 A1* | 3/2010 | Kashif | A61B 5/02154 600/485 |
| 2010/0204589 A1 | 8/2010 | Swoboda et al. | |
| 2012/0203122 A1* | 8/2012 | Kinrot | A61B 5/7246 600/506 |
| 2013/0310661 A1 | 11/2013 | Jedwab et al. | |
| 2014/0031712 A1 | 1/2014 | Herskovitz et al. | |
| 2014/0187992 A1 | 7/2014 | Wilmering | |
| 2014/0194740 A1 | 7/2014 | Stein | |
| 2014/0371545 A1* | 12/2014 | Ben-Ari | A61B 5/6814 600/301 |
| 2016/0081604 A1 | 3/2016 | Prasad et al. | |
| 2016/0278736 A1 | 9/2016 | Hamilton | |
| 2016/0287127 A1 | 10/2016 | Kesinger | |
| 2020/0085317 A1* | 3/2020 | Bushi | A61B 5/6803 |

OTHER PUBLICATIONS

Traian Damsa et al; Blood-Hammer phenomenon in Cerebral Hemodynamics, Mathematical Biosciences, Jan. 1, 1976, pp. 193-202, XP055686984.

Ioannis Christou et al; A Broad Diagnostic Battery for Bedside Transcranial Doppler to Detect Flow Changes with Internal Carotid Artery Stenosis or Occlusion, Journal of Neuroimaging, Jul. 31, 2001, pp. 236-242, XP055687360.

Andrew M Demchuk et al; Specific Transcranial Doppler Flow Findings related to the Presence and Site of Arterial, Occlusion, Stroke, vol. 31. No 1, Jan. 1, 2000, pp. 140-146, XP055687435.

\* cited by examiner

| Artery Name | Flow [ml/Min] | Wall thickness [mm] | Internal diameter [mm] | Velocity [cm/sec] | Sonic speed in the artery [m/sec] | F=C/gA | Elasticity modulus of the artery [pascal] | Transmission factor | Junction | Delta Pressure magnitude [mmHg] |
|---|---|---|---|---|---|---|---|---|---|---|
| MCA | 153 | 0.36 | 2.86 | 40 | 13.85 | 220082 | 1600000 | N.A | N.A | 43* |
| ACA | 79 | 0.29 | 2.34 | 30 | 13.74 | 326218 | 1600000 | 0.55 | MCA-ACA-Siphon | 23.4 |
| Siphon | 232 | 0.5 | 4 | 31 | 13.8 | 112120 | 1600000 | 0.94 | Siphon-PComA-Siphon | 22 |
| PCom/OPhA | 48 | 0.18 | 1.5 | 47 | 13.7 | 835801 | 1600000 | 0.78 | Siphon-OPhA-ICA | 17.2 |
| ICA | 280 | 0.5 | 4 | 37 | 9.8 | 79282 | 800000 | 0.31 | ICA-ECA-CCA | 5 |
| ECA | 120 | 0.38 | 4 | 16 | 8.5 | 69084 | 800000 | | | |
| CCA | 400 | 0.63 | 6.5 | 20 | 6.1 | 18677 | 400000 | | | |

FIG. 8 (Prior Art)

SYSTEM AND METHOD OF DETECTING INTER-VASCULAR OCCLUSION

CROSS-REFERENCE TO RELATED APPLICATIONS

This application is a National Phase Application of PCT International Application No. PCT/IL2017/051381, International Filing Date Dec. 25, 2017, claiming the benefit of U.S. Provisional Patent Application No. 62/439,037, filed Dec. 25, 2016, which is hereby incorporated by reference.

BACKGROUND OF THE INVENTION

Stroke is the fourth leading cause of death in the United States. Furthermore, stroke is the leading cause of serious long-term adult disability in the United States with approximately one third of patients are left dependent on others. Ischemic stroke that accounts for approximately 87% of all strokes is a result of a thrombotic or embolic occlusion of a cerebral artery. Ischemic strokes caused by proximal large vessel occlusions (LVO) such as proximal Middle Cerebral Artery (MCA) occlusion, are known to have high probability for causing severe disability.

The known and proven interventions treatments for acute ischemic stroke include: intravenous tissue plasminogen activator (IV tPA) recanalization therapy for eligible patients within 3 to 4.5 hours of onset, intra-arterial mechanical thrombectomy (MT) for patients within 6 hours of onset, aspirin to deter clot propagation for the remainder, and supportive care in a Stroke Unit/Stroke Center for all. Accordingly, the time from the actual onset to full diagnosis of the occlusion is very crucial. For a patient to enjoy the maximum benefits of IV tPA, the IV tPA must be given in the 60- to 90-minute window from the onset. A delay of more than 90-minute and the benefit is halved. Yet, typically patients are treated with tPA in actual practice more than 2.25 hours after onset, when the benefit is quite modest.

Time is a critical factor to achieve successful clinical outcomes for MT. It was found that early arrival to emergency department was associate with better collaterals, smaller established infarcts, and better clinical outcome after revascularization. Currently, diagnosis of strokes caused by LVO is done by a professional preforming clinical diagnoses in order to define a suspected LVO. The clinical diagnoses should be followed by a Computed Tomography Angiography (CTA). Such a full diagnosis requires evacuation of the patient to a hospital or a stroke center that has both trained professionals and an available CTA. Evacuation of a patient with suspected LVO to a hospital that does have CTA and/or MT unit may increase the chances of the patient to improve clinical outcome following stroke.

Accordingly, there is a need for a device and a method that may allow medics, paramedics and even the patients themselves to detect inter-vascular occlusion as soon as possible and as close as possible to the actual onset.

SUMMARY OF THE INVENTION

Some aspects of the invention may be directed to a method of determining an occurrence of inter-vascular occlusion. The method may include: receiving, from a first sensor, a first indication, related to blood flow in a first artery supplying blood to a first hemisphere of a subject's brain; receiving from one of: the first sensor and a second sensor, a second indication related to the blood flow in a second artery supplying blood to a second hemisphere of the subject's brain; comparing the first and second indications; and determining an occurrence of an inter-vascular occlusion based on the comparison.

In some embodiments, the first and second indications may include a first pressure waveform and a second pressure waveform. In some embodiments, the first and second indications may include a first reflected blood pressure wave and a second reflected blood pressure wave. In some embodiments, the first and second indications may include a first blood flow rate and a second blood flow rate. In some embodiments, the first and second indications may include a first blood flow velocity and a second blood flow velocity.

In some embodiments, determining the occurrence of the inter-vascular occlusion may include detecting a pressure hammer waves in one of the first artery and the second artery. In some embodiments, the first and second indication may include: a first amplitudes of a systolic blood pressure in the first artery and a second amplitudes of the systolic blood pressure in the second artery, and determining the occurrence of the inter-vascular occlusion may include detecting an increase in the amplitudes of the systolic blood pressure at one artery following the occurrence of the inter-vascular occlusion in comparison to the other.

In some embodiments, the first and second indication may include a first time duration for the diastolic peak in the first artery and a second time duration for the diastolic peak in the second artery, and determining the occurrence of the inter-vascular occlusion may include detecting a decrease in the time duration following the inter-vascular occlusion in one artery in comparison to the other. In some embodiments, the first and second indication may include a pulse wave velocity of the first artery and a pulse wave velocity of the second artery, and determining the occurrence of the inter-vascular occlusion comprises detecting an increase in the pulse wave velocity following the inter-vascular occlusion in one artery in comparison to the other.

In some embodiments, the first and second indications are the first ratio between the amplitudes of the forward and reflected first pressure waveform and the second ratio between the amplitudes of the forward and reflected second pressure waveform, and determining the occurrence of the inter-vascular occlusion may include detecting a raise in the ratio of one pressure waveform in comparison to the other. In some embodiments, the first and second indications are measurements of a first vascular impedance of the first artery and a second vascular impedance of the second artery, and determining the occurrence of the inter-vascular occlusion may include detecting an increase in the vascular impedance in the first arteries in comparison to the second arteries.

In some embodiments, the first indication and second indication are measurements of time delay between a forward blood pressure wave and a reflected blood pressure wave, and determining the occurrence of the inter-vascular occlusion may include detecting a decrease in the time difference between the forward and the reflected blood pressure waves at the first artery in comparison to the second artery. In some embodiments, the first indication and the second indication are calculations of mean reflection coefficient moduli of the first artery and the second artery, and determining the occurrence of the inter-vascular occlusion may include detecting an increase in the mean reflection coefficient modulus of the first artery in comparison to the second artery.

In some embodiments, the first indication and second indication may include the frequencies content of the first pressure waveforms and the frequencies content of the second pressure waveforms, and determining the occurrence of the inter-vascular occlusion comprises detecting an increase in at least some of frequencies of one waveform with respect to the other. In some embodiments, the first indication and second indication may include second order time derivatives of the first pressure waveform and the second pressure waveform, the second order time derivatives are for identifying a timing of a inflection point at each pressure waveform, and determining the occurrence of the inter-vascular occlusion may include detecting a reduction in the timing of the inflection point.

In some embodiments, the first indication and second indication may include augmentation indexes calculated from the first waveforms and the second pressure waveform, and determining the occurrence of the inter-vascular occlusion may include detecting a rise in the augmentation index of one pressure wave form in comparison to the other.

In some embodiments, the first sensor and the second sensor may include piezoelectric devices. In some embodiments, the first sensor and second sensor are pressure sensors. In some embodiments, the first sensor comprises an ultrasound transducer. In some embodiments, the first and second sensors may include sensors that measure a volume or diameter of the arteries.

Some aspects of the invention may be related to a system for determining an occurrence of an inter-vascular occlusion. The system may include one or more sensors configured to be located in proximity to a first artery that supplies blood to the first hemisphere of a subject's brain and to a second artery that supplies blood to the second hemisphere of the subject's brain; and a communication unit configured to send to a processor: a first indication, related to blood flow in a first artery supplying blood to a first hemisphere of a subject's brain; and a second indication, related to blood flow in a second artery supplying blood to a first hemisphere of a subject's brain.

In some embodiments, the system may include a wearable element for attaching the one or more sensors to a tissue in proximity to the first and second arteries. In some embodiments, the wearable element may include at least one of: stickers to attached a first and a second sensors to a skin of a user, one or more elastic strips to attached the first and second sensors to a skin of a user, a hat-like element, a necklace, a choker, a bandage, a scarf and a collar-like element.

In some embodiments, the system may include a controller configured to: receive, from a first sensor from the one or more sensors, the first indication; receive from one of: the first sensor and a second sensor from the one or more sensors, the second indication; compare the first and second indications; and determine the occurrence of the inter-vascular occlusion based on the comparison.

In some embodiments, the one or more sensors may include piezoelectric devices. In some embodiments, the one or more sensors are pressure sensors. In some embodiments, the one or more sensors may include an ultrasound transducer. In some embodiments, the one or more sensors comprise sensors that measure a volume of the arteries.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 8 include a table that describes the magnitudes of the pressure hammer waves at different arteries of the cerebral intracranial and extracranial vascular system following sudden occlusion of the MCA.

Figure 1:
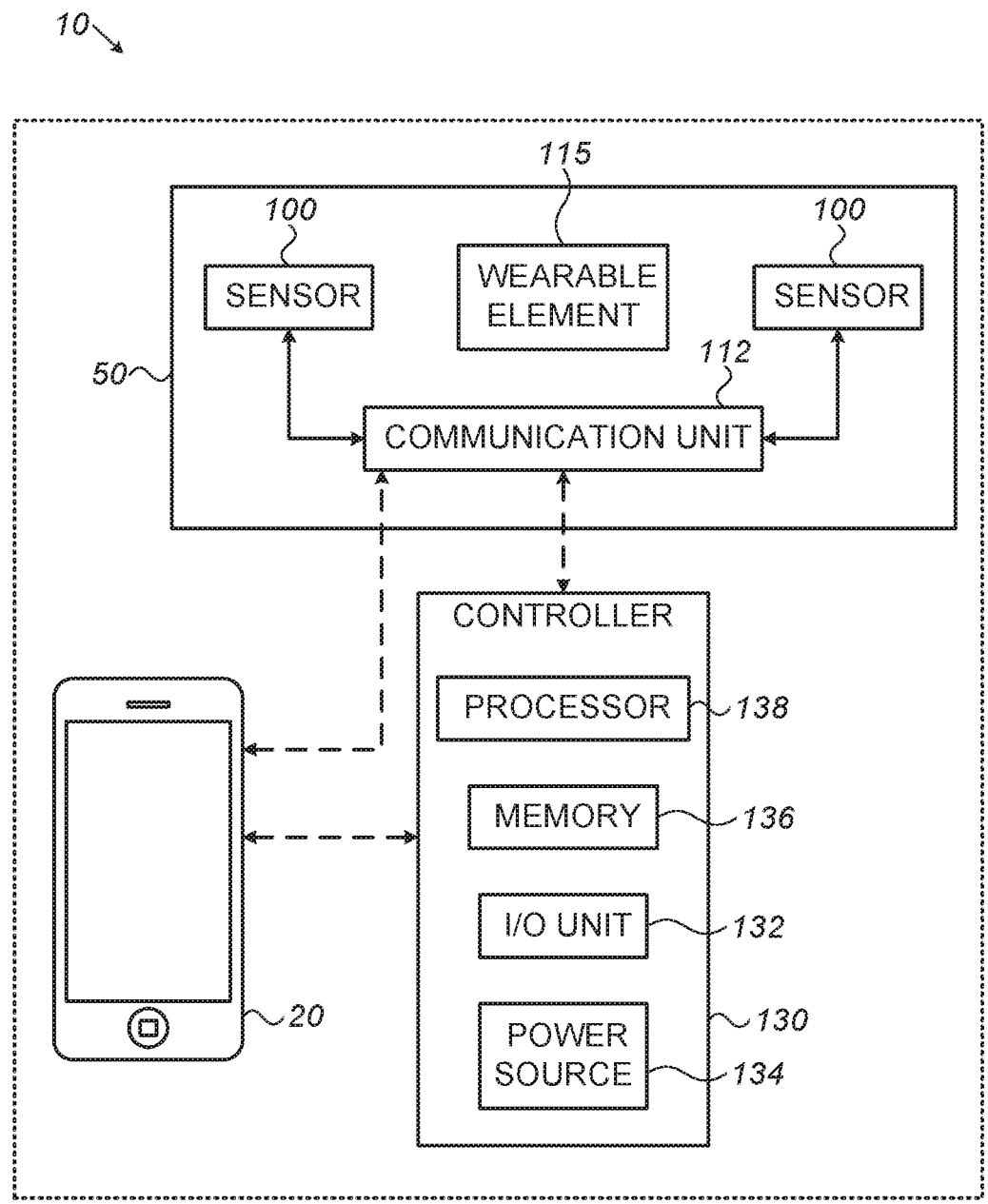
FIG. 1 is a high-level block diagram of a system for detecting an inter-vascular occlusion according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Some aspects of the present invention may be related to a device, a system and a method for determining an occurrence of an inter-vascular occlusion. A device and system according to embodiments of the invention may allow an early detection of large vessel occlusions (LVO) even at the patient's house or in the ambulance during a medical evacuation. Such a system and a device may allow dramatic time reduction from the occlusion onset to the provision of the required medical treatment. A patient being in a risk group for a stroke may wear the device according to some embodiments of the invention, for example, during sleeping hours or when he/she are left alone, and the device may alert (e.g., the patient, a family member, a caregiver and the like) when/if an inter-vascular occlusion has occurred. In such case the patient may be rushed to a hospital and may start to be provided to with a medical treatment, such as, IV tPA recanalization therapy for eligible patients within 3 to 4.5 hours of onset or intra-arterial MT for patients within 6 hours of onset.

Additionally or alternatively, a system and a device according to some embodiments of the invention may be included in an ambulance or in other Emergency Medical Services (EMS) and may be used by medics or paramedics to detect a potential LVO, thus may allow the medics or paramedics to rush the patient to a hospital or a Stroke center equipped with the required medical equipment, for example, intra-arterial mechanical thrombectomy unit and a CT.

Some embodiments of the invention may include comparing two signals measured near two different arteries supplying blood to the brain, one at each side of the head or neck, and determining based on the comparison the occurrence of the inter-vascular occlusion. Since the two compared signals are received from the same subject at substantially the same time (or with seconds from one another) the comparison is based on information related to the specific subject at a specific condition. According to some embodiments, there may be no need to compare the signals to any related data that was gathered from other subjects, as done in prior art methods. In some embodiments, a first sensor (e.g., a first piezo electric device) may be placed in proximity to, (e.g., on the skin proximal to an artery) a first artery supplying blood to a first hemisphere of the brain and a second sensor (e.g., a second piezo electric device) may be placed in proximity to (e.g., on the skin proximal to) a second artery supplying blood to a second hemisphere of the brain. In some embodiments, a first indication, related to blood flow in the first artery and a second indication, related to blood flow in the second artery may be received from the first and second sensors respectively. In some embodiments, the first and second sensors may include two ultrasound (US) transducers placed in proximity to the first and second arteries such the first and second indications may include first and second US signals acquired simultaneously. In some embodiments, the first and second indications may be received from a single sensor (e.g., an ultrasound (US) transducer). The single sensor may first be placed in proximity to the first artery for taking the first indication (e.g., a first US scan) and then be moved to be in proximity to the second artery for taking the second indication (e.g., a second US scan).

Reference is now made to FIG. 1 which is a high-level block diagram of a system 10 for determining an occurrence of inter-vascular occlusion according to some embodiments of the invention. System 10 may include a device 50 for determining an occurrence of inter-vascular occlusion and a controller 130. In some embodiments, controller 130 may be included in device 50 and/or may be a processing unit of a user device 20. User device 20 may be a desktop computer, a laptop commuter, a tablet, a smartphone, a smartwatch and the like. User device 20 may communicate with controller 130 using any know method for wired and/or wireless communication.

Device 50 may include one or more sensors 100 and a communication unit 112. One or more sensors 100 may include a strain gauge, a pressure sensor (e.g., the piezoelectric device illustrated and discussed with respect to FIG. 2), a velocity sensor, an US transducer, a Laser Doppler, a photoplethysmogram (PPG), a radar, an optical sensor, and the like. In some embodiments, one or more sensors 100 may include any sensor that is based on piezoresistivity or capacitance principles. In some embodiments, one or more sensors 100 may include any sensor capable of measuring the Palpable Carotid Pulse Pressure.

Figures 3A, 3B, 3C:
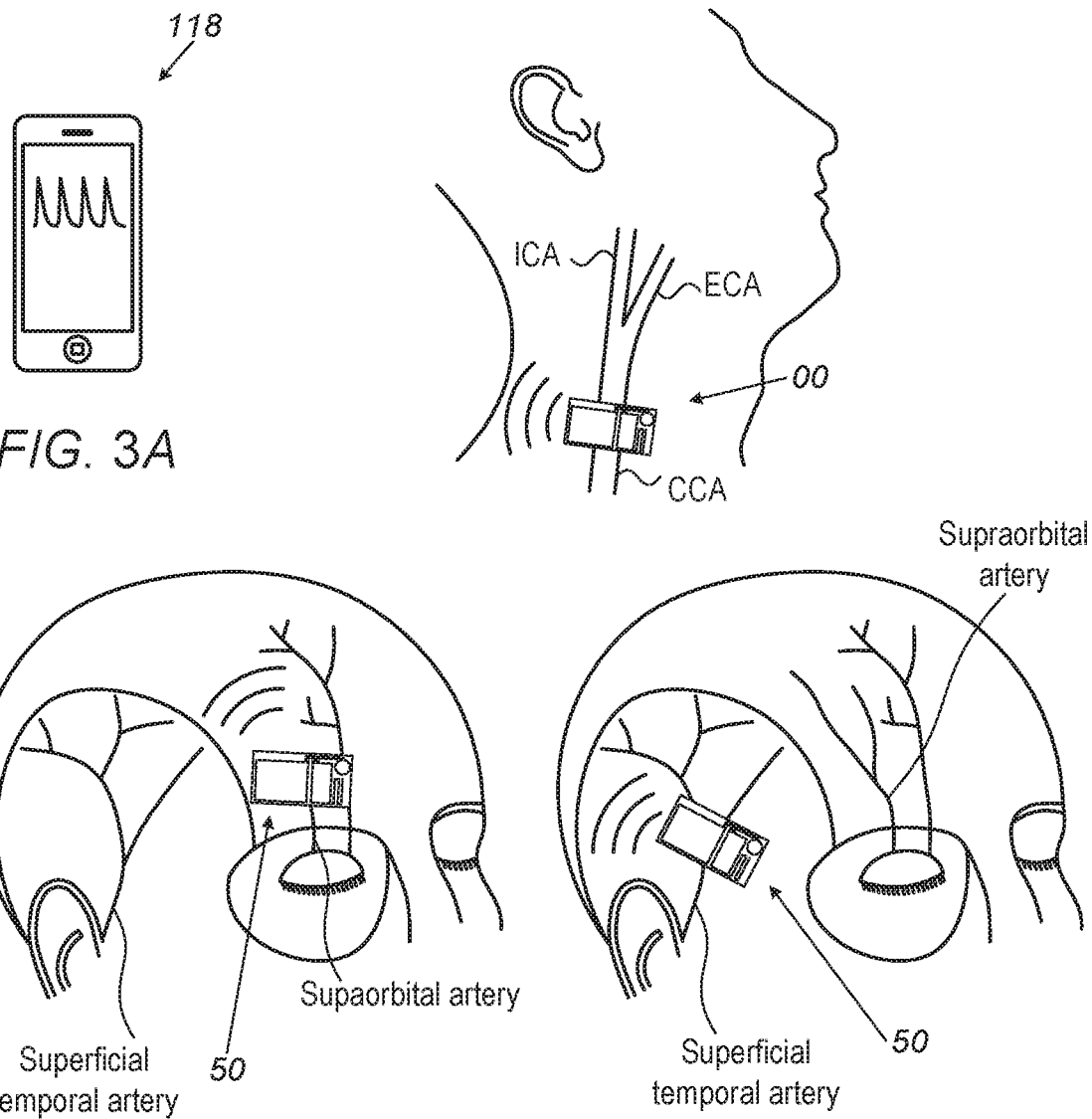
FIGS. 3A, 3B and 3C are illustrations of optional placement of the device for detecting inter-vascular occlusion according to some embodiments of the invention on a subject's head or neck.

In some embodiments, device 50 may further include a wearable element 115 for attaching one or more sensors 50 to a tissue in proximity to the first and second arteries. In some embodiments, wearable element 115 may include at least one of: medical adhesive patch to attach the first and second sensor to a skin of a subject (as illustrated in FIGS. 3A-3C), one or more elastic strips to attach the first and second sensor to a skin of a subject, a hat-like element, a collar-like element, a necklace, a choker, a bandage, a scarf and the like.

One or more sensors 100 may be configured to detect an indication, related to blood flow in an artery supplying blood to a hemisphere of a subject's brain. One or more sensors 100 may be configured to measure the pressure waveform (e.g., the cutaneous pressure wave form) of blood flow in the artery, the forward pressure waveform and/or the reflected pressure waveform, time delay between a forward blood pressure wave and a reflected blood pressure wave, the frequencies content of the pressure waveform (e.g., the frequencies of various harmonies forming the waveform), inflection point, a time of the diastolic peak, augmentation index, pulse wave velocity, ratio of the amplitudes of the backward (Pb) and forward (Pf) pressure components, any mathematical manipulation conducted on the measured pressure waveform, a velocity of the blood flowing in the artery, a vascular impedance of the artery, a diameter of the artery and the like.

Controller 130 may include a processor 138 that may be, for example, a chip or any suitable computing or computational device, a memory 136, any number of input/output units 132 and a power source 134. Processor 136 may include an operating system that may be or may include any code segment designed and/or configured to perform tasks involving coordination, scheduling, arbitration, supervising, controlling or otherwise managing operation of controller 130.

Memory 136 may be or may include, for example, a Flash memory, a volatile memory, a non-volatile memory, a cache memory, a buffer, a short-term memory unit, a long term memory unit, or other suitable memory units or storage units. Memory 136 may store any executable code, e.g., an application, a program, a process, task or script. The executable code may include instructions for determining an occurrence of inter-vascular occlusion or any other codes or instruction for executing methods according to embodiments of the present invention.

Input/output units 132 may include any applicable input/output (I/O) devices. For example, a screen, a touchscreen, a keyboard, a speaker, one or more buttons, a wired or wireless network interface card (NIC), a modem, printer or facsimile machine, a universal serial bus (USB) device or external hard drive may be included in input/output unit 132.

Power source 134, may be any battery or may include a socket for connecting to an electricity grid.

Figure 2:
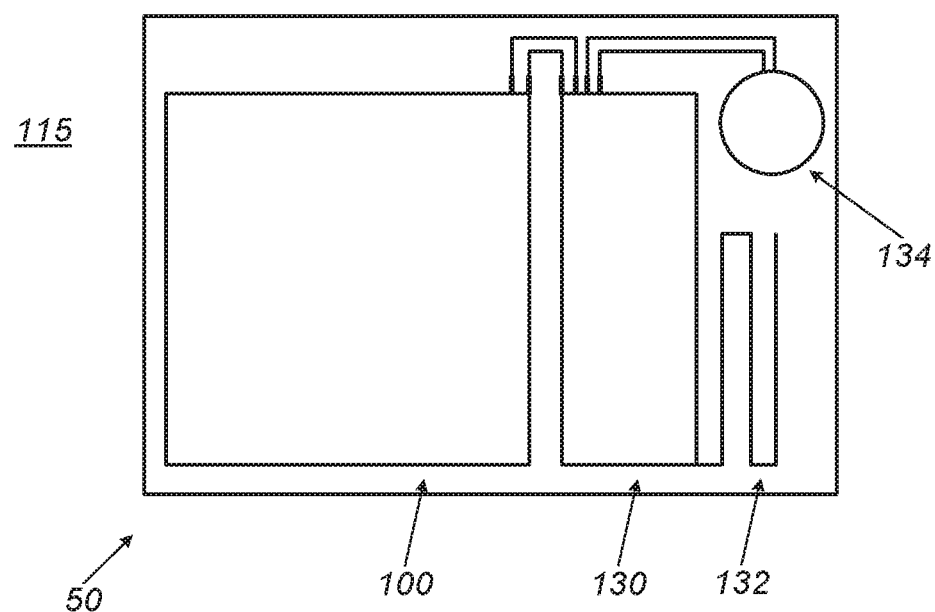
FIG. 2 is a schematic illustration of a device for detecting an inter-vascular occlusion non invasively according to some embodiments of the invention.

Reference is now made to FIG. 2 which is a schematic illustration of a device for detecting inter-vascular occlusion according to some embodiments of the invention. Device 50 may include one or more pressure sensors 100, controller 130, communication unit (e.g., antenna) 132 and power source (e.g., battery) 134. In some embodiments, all the elements of device 50 may be attached to a medical adhesive patch (e.g., a sticker) 115 or to any other element as disclosed above.

Reference is now made to FIGS. 3A, 3B and 3C which are illustrations of optional placements for one or more devices for detecting inter-vascular occlusion according to some embodiments of the invention on a subject's head and neck. In some embodiments, device 50 may include one or more sensors 100 that may be configured to monitor blood pressure changes in near-surface arteries. In some embodiments, two sensors 100 or two devices 50 may each be placed at corresponding locations on the skin from both sides of a subject's head or neck. FIGS. 3A-3C show only one half of the subject head and neck however substantially identical sensors 100 or devices 50 may be placed at corresponding locations on both sides of the subject's head or neck.

As illustrated in FIGS. 3A, 3B and 3C devices 50 may be attached using medical adhesive patch to a first side and a second side of the subjects head or neck in proximity to near-surface arteries. FIG. 3A is an illustration of device 50 attached to the neck on the skin proximal to the locations of the carotid arteries, FIG. 3B is an illustration of device 50 attached to a forehead of a subject on the skin proximal to the locations of the supraorbital arteries and FIG. 3C is an illustration of device 50 attached to the forehead on the skin proximal to the locations of the superficial temporal arteries.

Figure 4A:
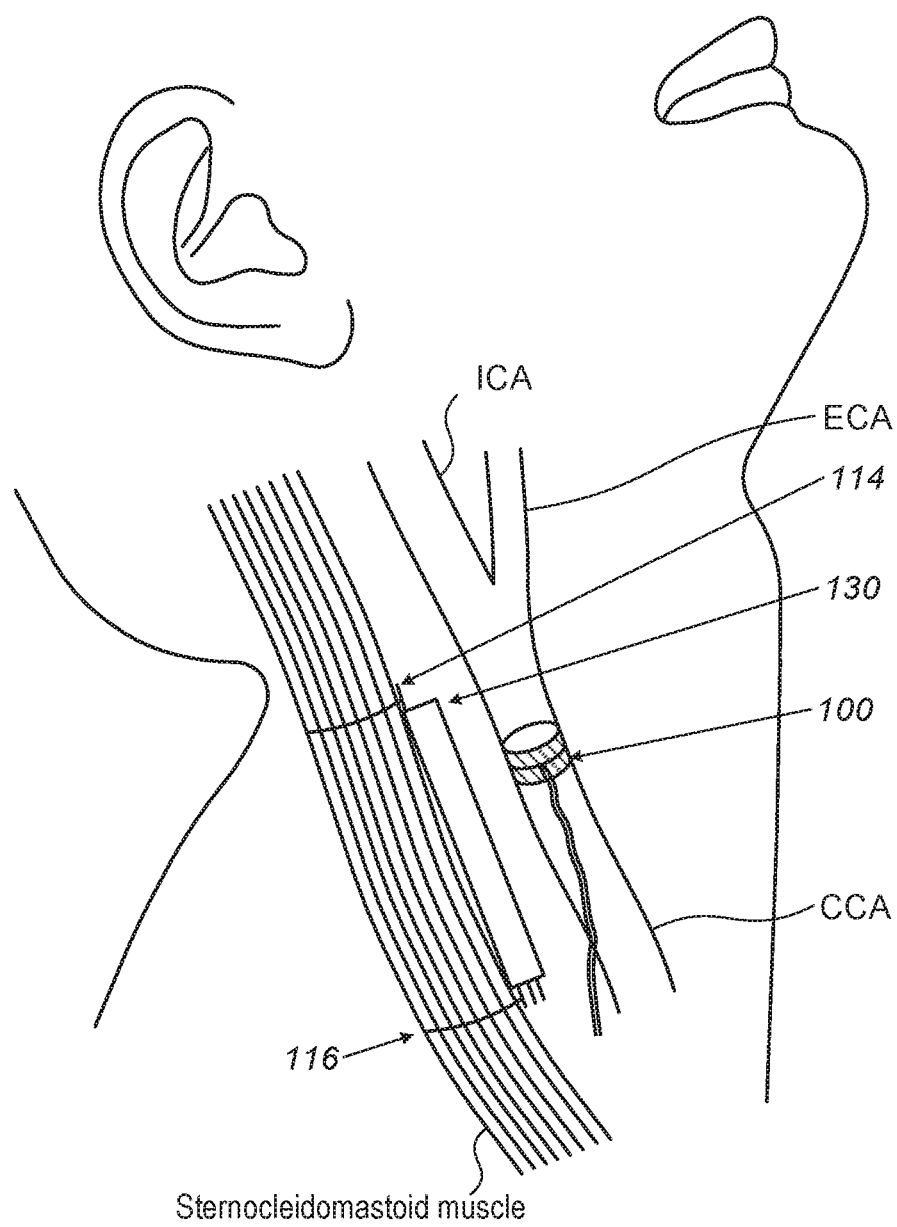
FIGS. 4A, 4B and 4C are illustration of the system for detecting an inter-vascular occlusion invasively according to some embodiments of the invention.
Figure 4B:
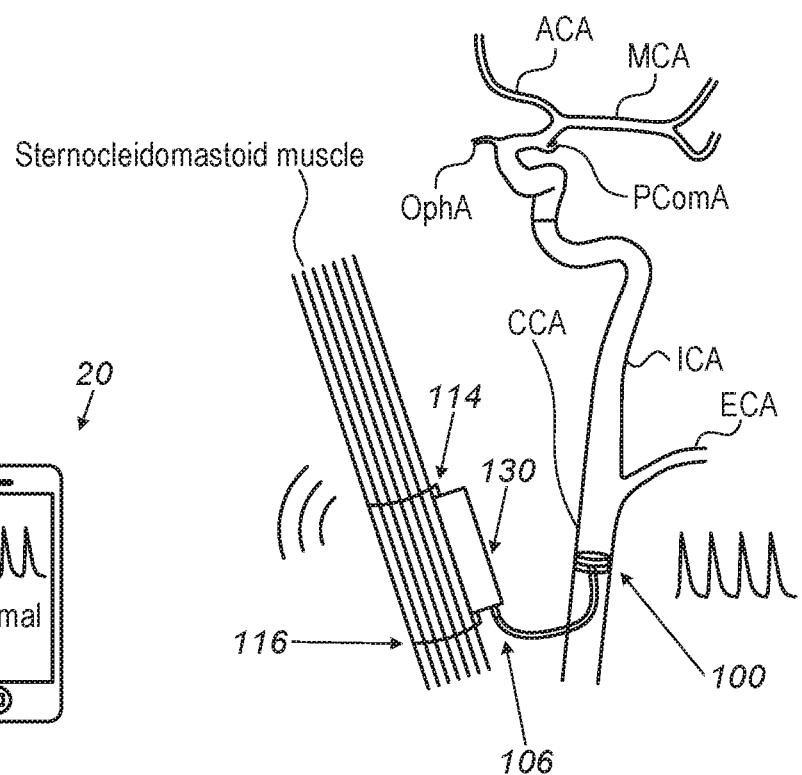
Figure 4C:
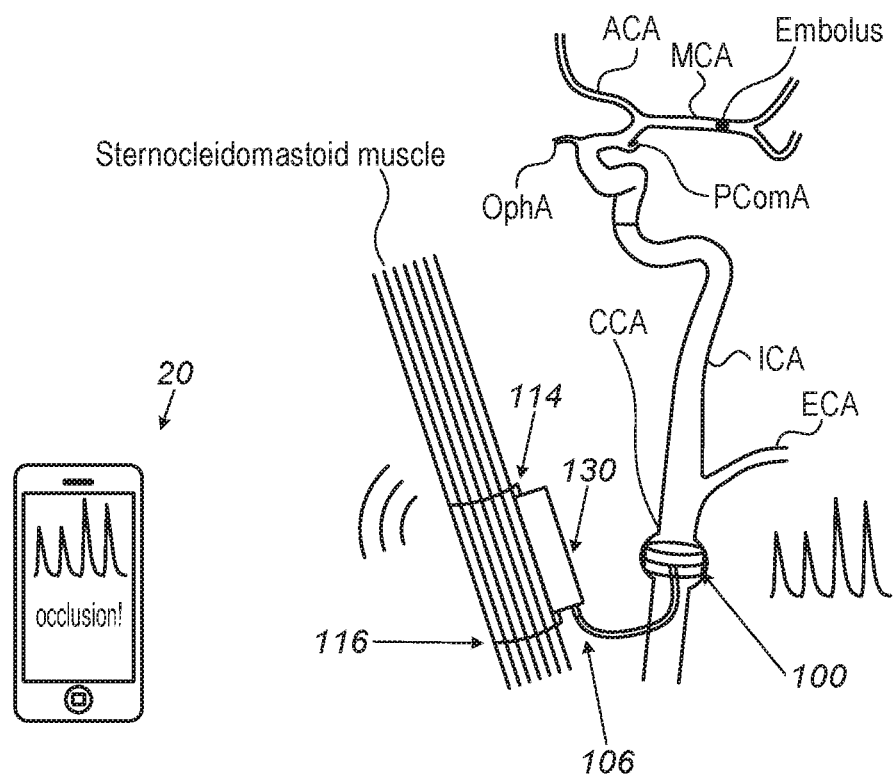

Reference is now made to FIGS. 4A, 4B and 4C which are illustrations of a system for in-vivo detecting inter-vascular occlusion according to some embodiments of the invention during an in-vivo procedure. System 10 may include a strain sensor 100 and a controller 130. In some embodiments, system 100 may include or may be in communication with user device 20. System 10 may further include surgical sutures 116 that may pass through special rings 114 for holding controller 130 to the sternocleidomastoid muscle. In some embodiments, system 10 may include electrical wires 106 for connecting sensor 100 to controller 130.

Strain sensor 100 (e.g., a strain gauge) may be configured to measure a change in a diameter of an artery and/or the pressure thereof. Sensor 100 may be placed in close proximity (touching or surrounding) to the carotid arteries and the sternocleidomastoid muscle, according to some embodiments of the invention, as illustrated in FIG. 4A. Such sensor can be wrapped around a common carotid artery (CCA) and/or an internal carotid artery (ICA). Under normal physiological conditions, illustrated in FIG. 4B, the sensor may measure normal pressure amplitudes in the CCA, as illustrated on the screen of user device 20. In case of artery occlusion (for example embolic occlusion in the MCA illustrated in FIG. 4C) or/and occlusion in extracranial arteries such as ICA, pressure amplitudes in the ICA and CCA may increase significantly, as illustrated on the screen of user device 20. In such cases an alert may be sent from the controller 130 to user device 20 or to a user interface included in I/O unit 132.

Figure 5:
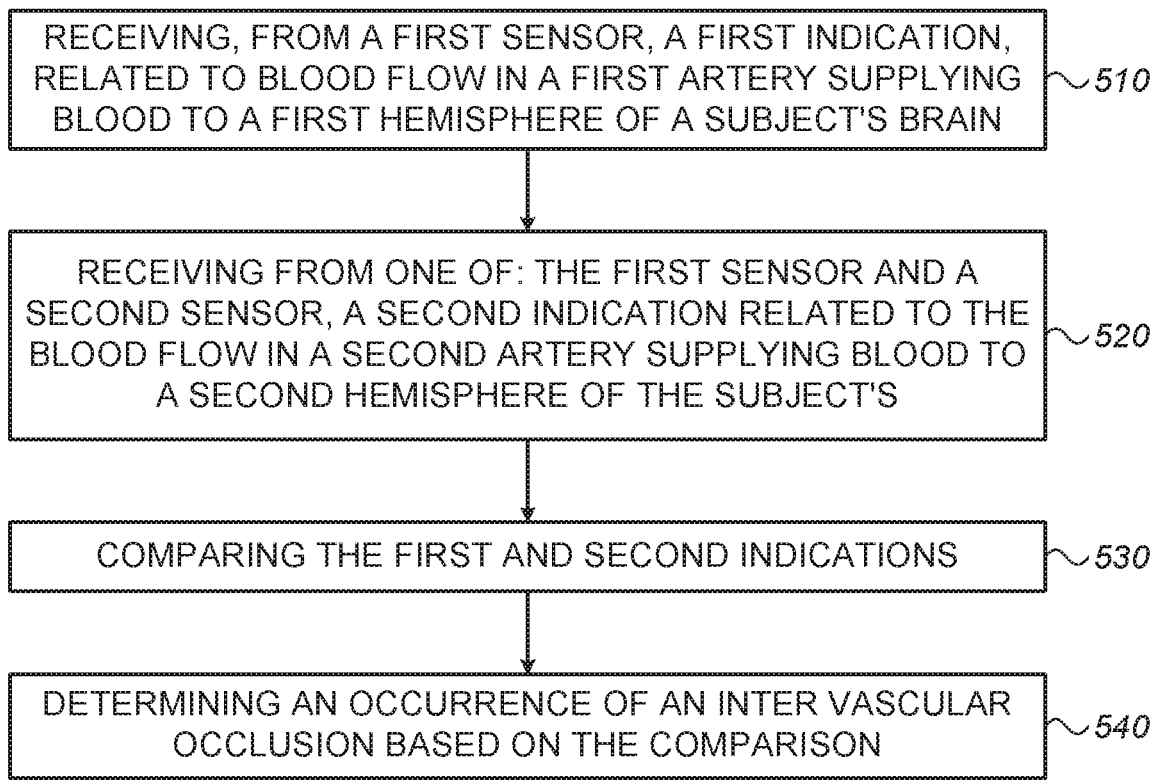
FIG. 5 is a flowchart of a method of detecting an inter-vascular occlusion according to some embodiments of the invention.

Reference is now made to FIG. 5 which is a flowchart of a method of determining an occurrence of inter-vascular occlusion according to some embodiments of the invention. The method of FIG. 5 may be performed by a processor such as processor 138 of controller 130, the processor of user device 20 or using any other suitable processor. In step 510, a first indication, related to blood flow in a first artery supplying blood to a first hemisphere of a subject's brain may be received from a first sensor. In step 520, a second indication, related to blood flow in a second artery supplying blood to a first hemisphere of a subject's brain may be received from a second sensor. In some embodiments, two devices such as devices 50 illustrated in FIG. 2 may each be placed at two sides of the subject's head or neck as illustrated in FIGS. 3A-3C. In some embodiments, two sensors being in communication with a single controller 130 may be placed at two different sides of the subject's head or neck in proximity (e.g., on the skin) to two corresponding arteries supplying blood to the brain. In some embodiments, sensor 100 of device 50 may detect the pressure waveform (e.g., the cutaneous pressure wave form) or blood flow waveform in the artery.

In some embodiments, an ultrasound transducer may first be placed in the first side of the subject's head or neck in proximity to the first artery supplying blood to the brain and a first ultrasound scan may be taken detecting one or more blood flow parameter (e.g. peak velocity, end-diastolic flow velocity and the like) in the first artery. The ultrasound transducer may be then relocated to the second side of the subject's head or neck in proximity to the second artery supplying blood to the brain and a second ultrasound scan may be taken from the second artery detecting one or more blood flow parameters in the second artery.

In some embodiments, the two signals may be the only data required for the determining of the occurrence of the inter-vascular occlusion. Therefore, no additional data, for example, stored in a database that was gathered from other subjects may be required. The comparison and determination may be conducted based on data related to a specific subject at a specific condition. The two compared signals may be received from the same subject at substantially the same time (or with seconds from one another) the comparison may be based on information related to the specific subject at the specific condition.

In some embodiments, information from previous measurements made to the same subject may be recorded and stored (e.g., may be determined as the baseline) to further be used for determining a threshold value for the comparison between the first and second indications. In some embodiments, information received from other subjects may also be used in order to determine the occurrence of an inter-vascular occlusion.

During inter-vascular occlusion at least one artery may be at least partially blocked by the occlusion. When an artery (e.g., large artery, such as, the ICA trunk, ICA trifurcation, MCA or small artery, such as, MCA branch) in the brain (or extracranial arteries like for example the CCA or ICA) is suddenly blocked (for example by an embolus that arises from elsewhere and suddenly blocks artery or by thrombotic occlusion), the local pressure in the ICA and CCA trunks rise due to both water-hammer phenomenon and increase in the brain vascular impedance. Water hammer phenomenon occurs when flow of fluid in a pipe is forced to stop by sudden closure at the end of the pipe. The kinetic energy of the fluid at the closure point is reduced to zero very rapidly, creating a high pressure at the closure point and causing a pressure wave to move upstream from it. The primary waves are followed by secondary ("bouncing") ones, until the fluid comes to rest. The brief upstream rise of pressure (Δp) at rapid closure of a valve may be calculated from equation 1:

$$\Delta P = V \rho C \tag{1}$$

Where ΔP is the brief upstream rise of pressure, V is the blood flow velocity, ρ is the blood's density and C the pulse wave velocity. C may be calculated using equation 2.

$$C = \frac{1}{\sqrt{\rho \left( K + \frac{d}{E\delta} \right)}} \tag{2}$$

Where K is the blood's compressibility, d is the internal diameter of the artery, δ is the artery's wall thickness and E is the elastic modulus of the artery.

In some embodiments, pressure rise following the water hammer effect may be calculated using equations (1) and (2). Assuming, for example, that blood flow velocity at the MCA is 0.39 m/s, the density of the blood is 1050 kg/m³, the compressibility of blood may be close to that of water, 4.8×10$^{(-10)}$ 1/Pa, internal diameter of the MCA is 2.86 mm and its wall thickness is 0.36 mm and elasticity modulus of the MCA is 1.6×10⁶ Pa the pressure increase ΔP during embolic occlusion may be calculated to be 43 mmHg A schematic illustration of the water hammer effect is given in FIGS. 6A and 6B.

Figure 6C:
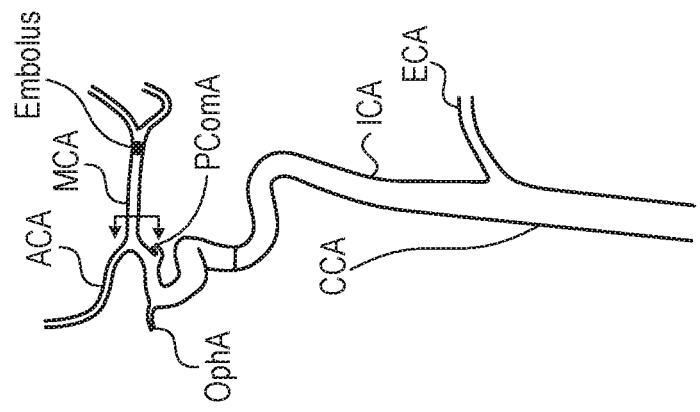
FIGS. 6A-6F are schematic illustrations of pressure waves in the anterior extracranial and intracranial vessels as a result of sudden middle cerebral artery occlusion and water hammer phenomenon.
Figure 6B:
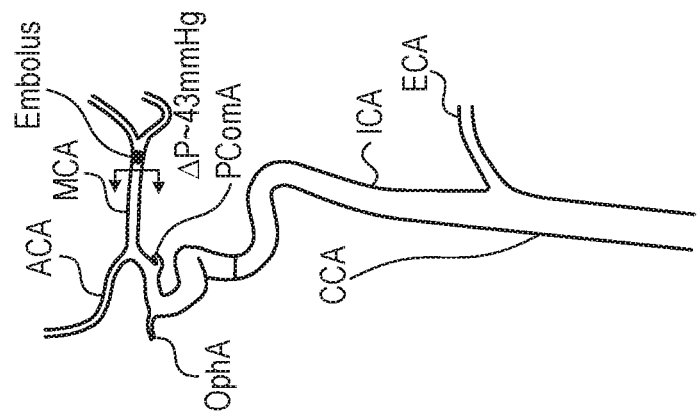
Figure 6A:
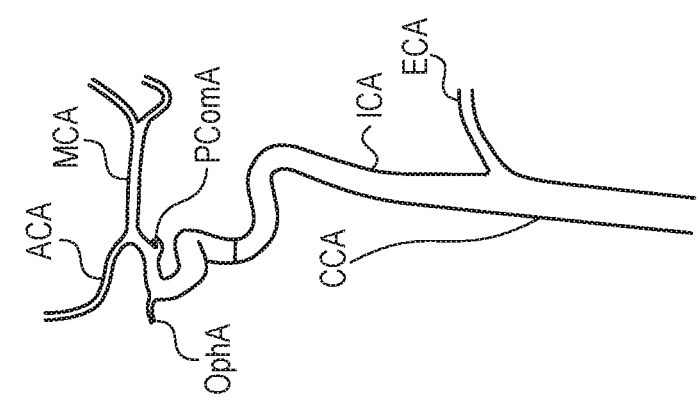

In some embodiments, the time of closure may not exceed twice the length of the upstream pipe divided by the velocity of sound in the blood in the artery, which can be calculated from the given data. If the MCA and carotid artery (e.g., 20 and 80 mm long respectively) are held as the upstream pipe, 8 millisecond (ms) may be sufficient for forming a water hammer effect. The pressure wave that may be generated near the occlusion may travel in the artery toward the MCA-ACA junction at sonic speed (as illustrated in FIG. 6C).

Figure 6F:
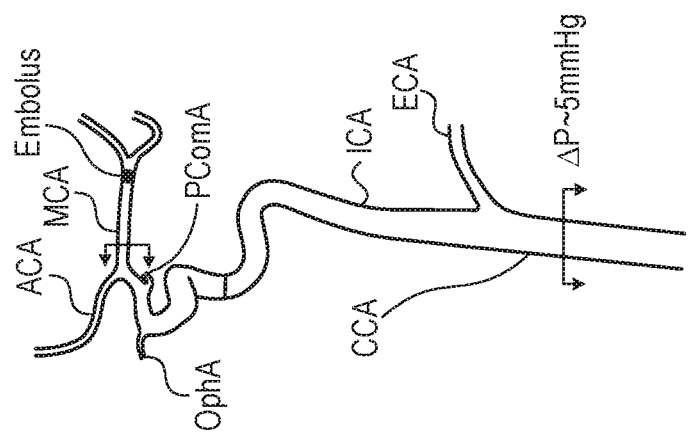
Figure 6E:
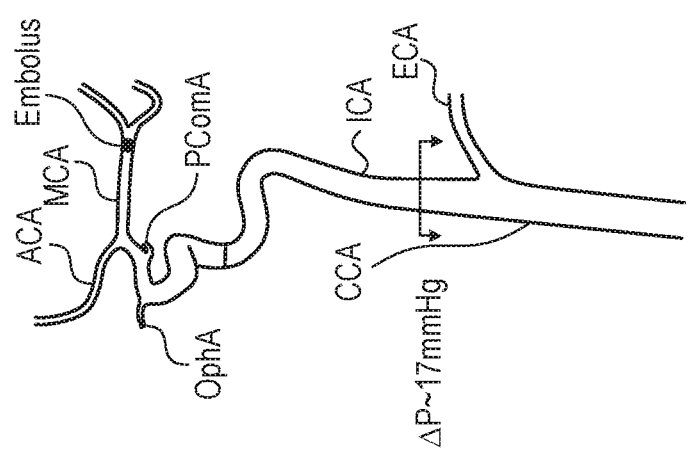
Figure 6D:
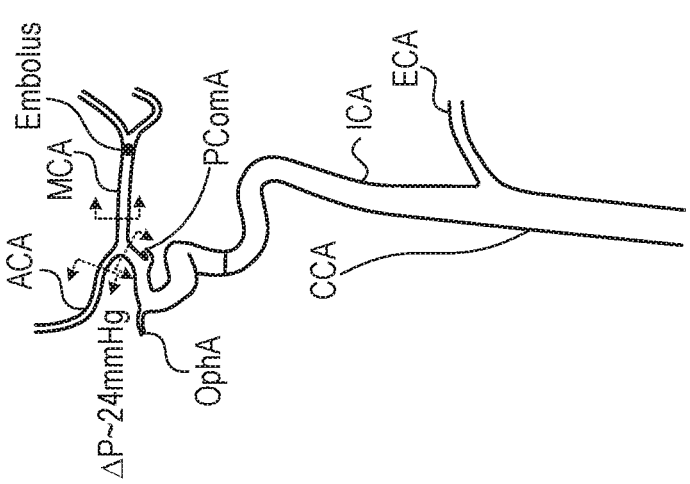

In some embodiments, when the pressure wave that was generated near the occlusion point arrived to the MCA-ACA junction it may be transmitted to the ACA and to the ICA siphon while part of it is reflected back, as illustrated in FIG. 6D. The effects of pipe junctions (as in arteries) on the pressure waves may be analyzed by employing a continuity of flow and continuity of pressure at the junctions.

Figure 7A:
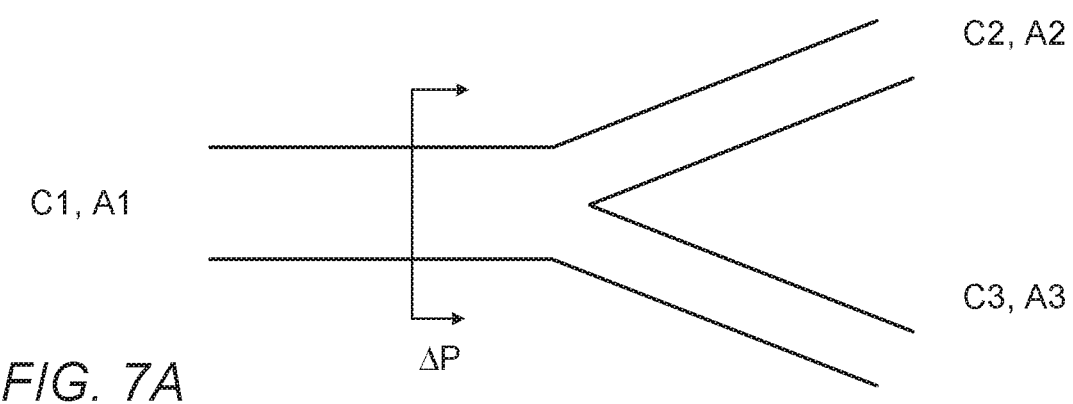
FIGS. 7A and 7B are schematic illustrations showing the effect of pipe junction on pressure wave.
Figure 7B:
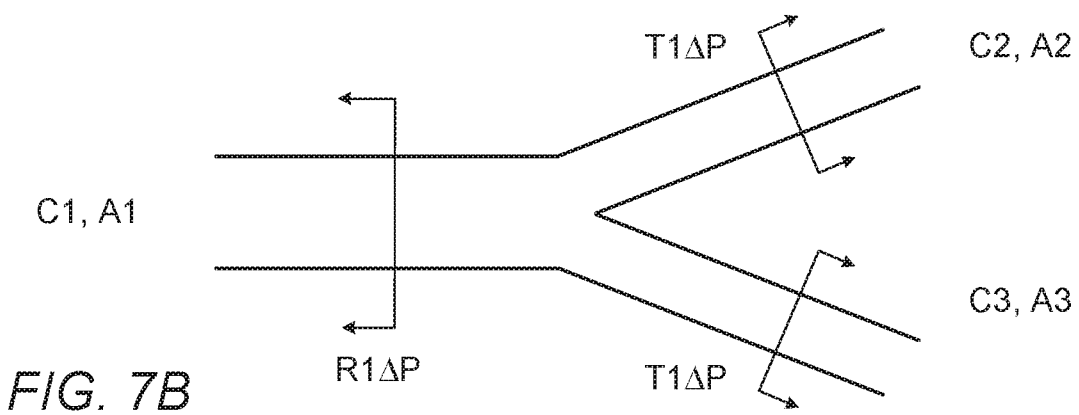

Referring now to FIGS. 7A and 7B which are schematic illustrations showing the effect of pipe junction on pressure waves. In some embodiments, a pressure wave of magnitude ΔP impinging in one of the junctions' legs, may be transmitted to each of the adjoining legs equally. The magnitude of the transmitted waves may be $T_1 \Delta P$ where the transmission coefficient, $T_i$, may be expressed using equation 3.

$$T_i = \frac{\frac{2}{F_i}}{\sum_j \left( \frac{1}{F_j} \right)} \tag{3}$$

Where F is calculated for each Ti using equation 4.

$$F = \frac{C}{gA} \tag{4}$$

Where A is the pipe cross section, g=9.8 m/sec² and C is the pulse wave velocity. In some embodiments, the summation j refers to all legs (pipes) connecting at a junction i. Accordingly, for the three pipe junctions illustrated in FIGS. 7A and 7B the transition factor may be calculated using equation 5.

$$T_1 = \frac{\frac{2}{F_1}}{\frac{1}{F_1} + \frac{1}{F_2} + \frac{1}{F_3}} \tag{5}$$

Using equation 5 and the data given in the table of FIG. 8 the transmission factor (Ti) for the MCA-ACA-siphon junction may be 0.55, therefore and the transmitted pressure wave to the siphon may be ~24 mmHg. The table in FIG. 8 describes the magnitudes of the pressure hammer waves at different arteries of the cerebral intracranial and extracranial vascular system following sudden occlusion of the MCA. MCA-middle cerebral artery, ACA-anterior cerebral artery, PCom-Posterior communicating, OPhA-Ophthalmic artery, ICA-internal carotid artery, ECA-external carotid artery, CCA-common carotid artery. The calculations are based on blood density=1050 [kg/m³], compressibility of blood=4.8×10$^{(-10)}$ [1/Pascal], g=9.8 [m/s²].

In the same manner, the magnitude of the transmitted pressure wave in the ICA trunk following the Posterior communicating artery (PComA) and ophthalmic artery (OPhA) junctions is ~17 mmHg (illustrated in FIG. 6E) and ~5 mmHg in the CCA (illustrated in FIG. 6F). In cases of total ICA occlusion or embolic occlusion in the ICA trifurcation the pressure's increase in the CCA and ICA trunks may be much higher.

In addition to water hammer effect, following artery occlusion (either in the brain or/and in the extracranial arteries, for example sudden occlusion of either the MCA, the ICA trunk or ICA trifurcation or smaller artery like MCA branch) the local blood pressure in the CCA and ICA rise as a result of an increase in the brain vascular impedance. The CCA supplies cerebral blood flow through the ICA and this vascular system normally has a low resistance vascular bed. Decrease in the CCA flow velocity has been reported in carotid occlusion, proximal MCA occlusion or severe stenosis by duplex ultrasonography.

In some embodiments, based on fluid dynamic it may be assumed that the decrease in the blood flow velocity in the CCA or ICA may be followed by an increase in the local blood pressure at the same locations. As known in the art, blood pressure wave is composed of a forward wave and a reflected wave. The forward wave is caused by blood flow coming from the constriction of the heart. The reflected wave is generated by the reflection of the forward wave at the peripheral arteries and it depends strongly on the viscoelastic properties of the vessel wall. The relationship between the spectrum components of the total P, forward $P_f$ and reflected $P_r$ blood pressure waves for the successive harmonics n of the heartbeat frequency in frequency domain can be expressed using equation 6.

$$P_n = P_{fn} + P_{rn} = P_{fn}(1+\Gamma_n) \quad (6)$$

where $$P_n = |P_n|e^{j\Theta_n}, P_{fn} = |P_{fn}|e^{j\Theta_{fn}}, P_{rn} = |P_{rn}|e^{j\Theta_{rn}}, \Gamma_n = |\Gamma_n|e^{j\gamma_n}$$

and where θ and γ are phase lag.

The reflection coefficient $\Gamma_n$ present in equation 6 can be calculated on the basis of the vascular input impedance $Z_n$ and the characteristic impedance $Z_{on}$ measured in a cross-section of the artery using equation 7.

$$\Gamma_n = \frac{P_{rn}}{P_{fn}} = \frac{Z_n - Z_{on}}{Z_n + Z_{on}} = |\Gamma_n|e^{j\gamma_n}$$

The input $\Gamma_n$ and characteristic $\Gamma_{on}$ impedances as function of the frequency are defined using equations 8.

$$Z_n = \frac{P_n}{Q_n} = |Z_n|e^{j\varphi_n}, \quad (8)$$

$$Z_{on} = \frac{P_{fn}}{Q_{fn}} = |Z_{on}|e^{j\varphi_n}$$

where φ and φ are phase lag where $P_n$, $P_{fn}$, are spectrum components of the total and forward blood pressure waves, $Q_n$, $Q_{fn}$ are spectrum components of the total and forward blood flow rates. According to equation 7 the spectrum components $P_{fn}$ and $P_{rn}$ of the forward and reflected blood pressure waves are calculated for the successive harmonics n of the heartbeat frequency using equations 9.

$$P_{fn} = \frac{P_n}{1+\Gamma_n} = |P_{fn}|e^{j\theta_{fn}}, \quad (9)$$

$$P_{rn} = P_n - P_{fn} = |P_{rn}|e^{j\theta_{rn}}$$

Where the components $P_{fn}$ and $P_{rn}$ may be the basis for determination of the course of the forward and reflected blood pressure waves in time domain. The characteristic impedance can be determined using equation 10.

$$Z_{on} = \frac{\rho c}{\pi R^2 \sqrt{(1-\sigma^2)M'_{10n}}} e^{-j\frac{\varepsilon_{10n}}{2}} \quad (10)$$

Where ρ is the blood density, R is the artery radius, σ is the Poisson constant, $M'_{10n}$ and $\varepsilon_{10n}$ are values which are functions of the artery radius, blood viscosity and harmonics n of the heartbeat frequency, C is the pulse wave velocity. In prior studies it was shown that compressing the brachial artery at a distance of 12 cm from the measuring point, the time delay between the reflected and forward waves has been reduced from 132 ms to 35 ms and the value of the mean reflection coefficient modulus has increased from 0.4398 to 0.7983. The studies further showed, a 60% reduction in the volumetric blood flow, an increase in the total pressure amplitude and changes in the shape of the total pressure waveform following the compression of the brachial artery. Some studies showed that an increase of the degree of stenosis of the ICA is also accompanied by an increase in the values of the input impedance, the mean reflection coefficient modulus and decrease in the time delay of the reflected blood pressure wave relative to the forward blood pressure wave as measured in the CCA. In addition, higher degree of stenosis caused a decrease in the CCA flow velocity and increase in the blood pressure that was measured in the CCA. In the case of critical stenosis, or occlusion of the ICA, the mean reflection coefficient modulus was greater by about 48% than in the case of the healthy persons.

In yet another study an occlusion of either the distal aorta or bilateral occlusion of the femoral arteries doubled the pressure augmentation that was measured in the ascending aorta. Accordingly, it is expected that following artery occlusion, such as, for example, sudden embolic occlusion of either the ICA trunk, the ICA trifurcation, the MCA or smaller artery, like MCA branch, the pressure augmentation of the CCA may be increase and the he cerebral impedance is also expected to increase. Due to the increase in the cerebral impedance, the pressure reflection coefficient may increase and also the part of the reflected pressure waves. As a consequence, it is expected that following the artery occlusion the amplitudes of the pressure waveforms in the affected ICA and CCA may increase and the shape of the waveform may change. In addition, due to the increase in the ICA pressure following artery occlusion (either in the brain or/and in the extracranial arteries) there may also be a potential local increase in blood pressure levels in the sub branches of the ICA (e.g., the supraorbital artery and its anastomosis the superficial temporal artery).

As known in the art, changes of the blood pressure in the arteries, such as, CCA and ICA may be correlated with variations of their external diameters. Therefore, according to some embodiments of the invention, it may be possible to use the pressure-diameter correlation in these vessels as the basis for a long-term, continuous monitoring of blood pressure. The diameter changes may be measured using a stain sensor such as sensor 100 that is being bilaterally wrapped around either the CCA or ICA (as illustrated in FIGS. 4A-4C) and detects changes in these arteries diameters.

In some embodiments, the first and second indications may include: a first blood pressure wave and a second blood pressure wave, any mathematical manipulation or data that may be received from analyzing the first blood pressure wave and a second blood pressure wave or other parameters such as blood flow rate and blood flow velocities that may be received from Doppler measurements conduct using, for example, an ultrasound transducer. In some embodiments, analyzing the first blood pressure wave and the second blood pressure wave may include conducting Fourier transform methods or fast Fourier transform (FFT) on the waveforms, taking second and forth order time derivatives of the blood pressure waveforms, analyzing the amplitude, flowrate, harmonies (frequency range) or any other characteristic of the blood pressure waves. In some embodiments, the characteristic of the blood pressure waves may be determined using any one of equations (1)-(10).

In some embodiments, the first and second indications may be taken from the same artery at two different points in time. In some embodiments, device 50 may be placed (e.g., attached) in proximity to a single artery and sensor 100 may send to controller 130 two or more indications related to the blood flow in the artery (e.g., any one of the indications disclosed herein) at two or more points in time. In some embodiments, sensor 100 may continuously send indications during a period of time.

In operation 530, the first and second indications may be compared and an occurrence of an inter-vascular occlusion may be determined based on the comparison, in operation 540. Some examples for the use of the method of FIG. 5 for determining an occurrence of an inter-vascular occlusion based on several types of indications related to blood flow in an artery are given herein. The first and second indications may be indications received from sensor(s) placed at two sides of the subject's head or neck, and/or from the same sensor at two points in time.

In some embodiments, the first and second indications may include a first blood flowrate and a second blood flowrate. In some embodiments, following an inter-vascular occlusion at the first artery a decrease in the flowrate may be detected. Accordingly, the comparison between the normal flowrate in the second artery and the slower flowrate in the first artery may yield to the determining of optional inter-vascular occlusion at the first artery.

In some embodiments, the first and second indications may include a first blood flow velocity and a second blood velocity. In some embodiments, following an inter-vascular occlusion at the first artery a decrease in the blood flow velocity may be detected. Accordingly, the comparison between the normal velocity in the second artery and the lower velocity in the first artery may yield to the determining of optional inter-vascular occlusion at the first artery.

In some embodiments, the first and second indications may include a first reflected blood pressure wave and a second reflected blood pressure wave. In some embodiments, following an inter-vascular occlusion at the first artery an increase in the amplitude and/or the velocity of the reflected wave may be detected. Accordingly, the comparison between the two reflected blood pressure waves may yield to the determining at which side of the brain an artery may have been blocked, or partially blocked.

In some embodiments, when the subject continuously wearing one or more devices 50 (for example during sleeping hours) a brief upstream rise of pressure ($\Delta p$) may be detected by one of the sensors indicating a water hammer phenomenon following an inter-vascular occlusion. The water hammer effect may also be detected by detecting raise in the impedance Z. Accordingly, an alert may be sent to a caregiver or a health service provider and the subject may be given a treatment less than 90 minutes from the onset of the inter-vascular occlusion.

In some embodiments, wherein the first and second indications may be measurements of a first vascular impedance of the first artery and a second vascular impedance of the second artery. In some embodiments, determining the occurrence of the inter-vascular occlusion in the first artery may include detecting an increase in the vascular impedance Z in the first arteries in comparison to the second arteries.

In some embodiments, the first indication and second indication may be measurements of time delay between a forward blood pressure wave and a reflected blood pressure wave. As disclosed above a decrease in the time delay of the reflected blood pressure wave relative to the forward blood pressure wave may be detected following an inter-vascular occlusion. Accordingly, determining the occurrence of the inter-vascular occlusion at the first artery may include detecting a decrease in the time difference between the forward and the reflected blood pressure waves at the first artery in comparison to the second artery.

In some embodiments, the first indication and the second indication may be calculations of mean reflection coefficient moduli $\Gamma_n$ (calculated, for example, using equation (7)) of the first artery and the second artery. In some embodiments, determining the occurrence of the inter-vascular occlusion at the first artery may include detecting an increase in the mean reflection coefficient modulus of the first artery in comparison to the second artery.

In some embodiments, wherein the first indication and second indication may include the frequencies content of the first pressure waveform and the frequencies content of the second pressure waveform. Each one of the first and second pressure waveforms may include a superposition of several harmonies each having a frequency. Accordingly, the frequencies content in a pressure waveform are the frequencies of the harmonies. The frequencies may be extracted from the pressure waveforms applying, for example, FFT methods. In some embodiments, determining the occurrence of the inter-vascular occlusion may include detecting an change in at least some of frequencies of one waveform with respect to the other.

In some embodiments, the first indication and second indication may include second order time derivatives of the first pressure waveform and the second pressure waveform. The second order time derivatives may identify the timing to the inflection point at each pressure waveform. In some embodiments, determining the occurrence of the inter-vascular occlusion may include detecting a reduction in the timing to the inflection point of one pressure wave form in comparison to the other.

In some embodiments, the first indication and second indication may include augmentation indexes calculated from the first pressure waveforms and the second pressure waveform. The augmentation index is the ratio between augmentation pressure and the pulse pressure. The augmentation pressure may be define as the pressure difference between the first and the second inflection point in a waveform. The pulse pressure may be defined as the pressure difference between the systolic blood pressure and the diastolic blood pressure. The augmentation index is expected to rise following an inter-vascular occlusion. Accordingly, determining the occurrence of the inter-vascular occlusion may include detecting a rise in the augmentation index of one pressure waveform in comparison to the other.

In some embodiments, the first and second indications may be a first ratio between the amplitudes of the forward and reflected first pressure waveform ($P_r/P_f$) and a second ratio between the amplitudes of the forward and reflected second pressure waveform. In some embodiments, determining the occurrence of the inter-vascular occlusion may include detecting a raise in the amplitudes' ratio of one pressure waveform in comparison to the other.

In some embodiments, the first and second indication may further include: a first amplitude of a systolic blood pressure in the first artery and a second amplitude of the systolic blood pressure in the second artery. In some embodiments, determining the occurrence of the inter-vascular occlusion may include detecting an increase in the amplitudes of the systolic blood pressure at one artery following the occurrence of the inter-vascular occlusion in comparison to the other.

In some embodiments, the first and second indication may include a first time interval until the diastolic peak in the first artery and a second time interval until the diastolic peak in the second artery. In some embodiments, determining the occurrence of the inter-vascular occlusion may include detecting a decrease in the time interval following the inter-vascular occlusion in one artery in comparison to the other.

In some embodiments, the first and second indication may include a pulse wave velocity (PWV) of the first artery and a pulse wave velocity of the second artery. PWV may be measured in various segments of the arterial circulation. When two pressure waves are recorded at two different sites of the vascular tree, it is possible, owing to the propagation of the waves, to measure the time delay (t) and the distance (D) between these two waves. PWV may be defined using equation 11.

$$PWV=D/t \tag{11}$$

Measurement of time delay may be performed by determination of a foot-to-foot transit time. The term transit time, further to its regular meaning, may refer to the time between the beginning of the deflection corresponding to systole pressure wave that is measured in one point on the body and the pressure wave that is measured in second adjacent point in the same cycle.

In some embodiments, determining the occurrence of the inter-vascular occlusion may include detecting an increase in the pulse wave velocity following the inter-vascular occlusion in one artery in comparison to the other.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method of determining an occurrence of inter-vascular occlusion, comprising:
   receiving, from a first sensor, a first indication, related to blood flow in a first artery supplying blood to a first hemisphere of a subject's brain;
   receiving from one of: the first sensor and a second sensor, a second indication related to the blood flow in a second artery supplying blood to a second hemisphere of the subject's brain;
   comparing the first and second indications; and
   determining an occurrence of an inter-vascular occlusion based on the comparison;
   wherein the first and second indications are a first ratio between amplitudes of a forward and reflected first pressure waveform and a second ratio between amplitudes of a forward and reflected second pressure waveform, and
   wherein determining the occurrence of the inter-vascular occlusion comprises detecting a rise in the ratio of one pressure waveform in comparison to the other.

2. The method of claim 1, wherein the first and second indications comprise a first pressure waveform and a second pressure waveform.

3. The method of claim 1, wherein the first and second indications comprise a first reflected blood pressure wave and a second reflected blood pressure wave.

4. The method of claim 1, wherein the first and second indications comprise at least one of:
   a first blood flow rate and a second blood flow rate; and
   a first blood flow velocity and a second blood flow velocity.

5. The method of claim 1, wherein determining the occurrence of the inter-vascular occlusion comprises detecting a pressure hammer waves in one of the first artery and the second artery.

6. The method of claim 1,
   wherein the first and second indication include: a first amplitudes of a systolic blood pressure in the first artery and a second amplitudes of a systolic blood pressure in the second artery, and
   wherein determining the occurrence of the inter-vascular occlusion comprises detecting an increase in the amplitudes of the systolic blood pressure at one artery following the occurrence of the inter-vascular occlusion in comparison to the other.

7. The method of claim 1,
   wherein the first and second indication comprises a first time duration for a diastolic peak in the first artery and a second time duration for the diastolic peak in the second artery, and
   wherein determining the occurrence of the inter-vascular occlusion comprises detecting a decrease in the time duration following the inter-vascular occlusion in one artery in comparison to the other.

8. The method of claim 1,
   wherein the first and second indication comprises a pulse wave velocity of the first artery and a pulse wave velocity of the second artery, and
   wherein determining the occurrence of the inter-vascular occlusion comprises detecting an increase in the pulse wave velocity following the inter-vascular occlusion in one artery in comparison to the other.

9. The method of claim 1, wherein the first and second indications are measurements of a first vascular impedance of the first artery and a second vascular impedance of the second artery,
   and wherein determining the occurrence of the inter-vascular occlusion comprises detecting an increase in the vascular impedance in the first arteries in comparison to the second arteries.

10. A method of determining an occurrence of inter-vascular occlusion, comprising:
    receiving, from a first sensor, a first indication, related to blood flow in a first artery supplying blood to a first hemisphere of a subject's brain;
    receiving from one of: the first sensor and a second sensor, a second indication related to the blood flow in a second artery supplying blood to a second hemisphere of the subject's brain;
    comparing the first and second indications; and
    determining an occurrence of an inter-vascular occlusion based on the comparison,
    wherein the first indication and second indication are measurements of time delay between a forward blood pressure wave and a reflected blood pressure wave, and
    wherein determining the occurrence of the inter-vascular occlusion comprises detecting a decrease in the time difference between the forward and the reflected blood pressure waves at the first artery in comparison to the second artery.

11. A method of determining an occurrence of inter-vascular occlusion, comprising:
    receiving, from a first sensor, a first indication, related to blood flow in a first artery supplying blood to a first hemisphere of a subject's brain;
    receiving from one of: the first sensor and a second sensor, a second indication related to the blood flow in a second artery supplying blood to a second hemisphere of the subject's brain;
    comparing the first and second indications; and
    determining an occurrence of an inter-vascular occlusion based on the comparison,
    wherein the first indication and the second indication are calculations of mean reflection coefficient moduli of the first artery and the second artery, and wherein determining the occurrence of the inter-vascular occlusion comprises detecting an increase in the mean reflection coefficient modulus of the first artery in comparison to the second artery.

12. The method of claim 2, wherein the first indication and second indication comprise frequencies content of the first pressure waveforms and frequencies content of the second pressure waveforms, and wherein determining the occurrence of the inter-vascular occlusion comprises detecting an increase in at least some of frequencies of one waveform with respect to the other.

13. A method of determining an occurrence of inter-vascular occlusion, comprising:

receiving, from a first sensor, a first indication, related to blood flow in a first artery supplying blood to a first hemisphere of a subject's brain;

receiving from one of: the first sensor and a second sensor, a second indication related to the blood flow in a second artery supplying blood to a second hemisphere of the subject's brain;

comparing the first and second indications; and determining an occurrence of an inter-vascular occlusion based on the comparison, wherein determining the occurrence of the inter-vascular occlusion comprises detecting a pressure hammer waves in one of the first artery and the second artery, wherein the first indication and second indication comprise second order time derivatives of the first pressure waveform and the second pressure waveform, the second order time derivatives are for identifying a timing of a inflection point at each pressure waveform; and wherein determining the occurrence of the inter-vascular occlusion comprises detecting a reduction in the timing of the inflection point.

14. A method of determining an occurrence of inter-vascular occlusion, comprising:

receiving, from a first sensor, a first indication, related to blood flow in a first artery supplying blood to a first hemisphere of a subject's brain;

receiving from one of: the first sensor and a second sensor, a second indication related to the blood flow in a second artery supplying blood to a second hemisphere of the subject's brain;

comparing the first and second indications; and determining an occurrence of an inter-vascular occlusion based on the comparison, wherein determining the occurrence of the inter-vascular occlusion comprises detecting a pressure hammer waves in one of the first artery and the second artery, wherein the first indication and second indication comprise augmentation indexes calculated from the first waveforms and the second pressure waveform, and wherein determining the occurrence of the inter-vascular occlusion comprises detecting a rise in the augmentation index of one pressure wave form in comparison to the other.

* * * * *